United States Patent
Schneider

(10) Patent No.: US 8,049,165 B2
(45) Date of Patent: Nov. 1, 2011

(54) SALIVA ASSAY TECHNIQUE FOR HEAVY METAL

(75) Inventor: David Schneider, Troy, MI (US)

(73) Assignee: Coventry Diagnostics LLC, Troy, MI (US)

( * ) Notice: Subject to any disclaimer, the term of this patent is extended or adjusted under 35 U.S.C. 154(b) by 616 days.

(21) Appl. No.: 11/678,769

(22) Filed: Feb. 26, 2007

(65) Prior Publication Data

US 2008/0173806 A1 Jul. 24, 2008

Related U.S. Application Data

(60) Provisional application No. 60/776,626, filed on Feb. 24, 2006.

(51) Int. Cl.
*H01J 49/26* (2006.01)
*G01N 31/22* (2006.01)
*G01N 33/48* (2006.01)

(52) U.S. Cl. ...... 250/282; 250/281; 73/61.41; 73/61.42; 436/73; 436/77

(58) Field of Classification Search ............. 250/281, 250/282; 73/61.41, 61.42; 436/73, 74, 75, 436/76, 77, 78, 79, 80, 81, 82, 83, 84
See application file for complete search history.

(56) References Cited

U.S. PATENT DOCUMENTS

| 2005/0218319 A1* | 10/2005 | Bandura et al. ............... 250/288 |
| 2006/0018800 A1* | 1/2006 | Slowey et al. ................. 422/102 |
| 2006/0275801 A1* | 12/2006 | Henkin ............................. 435/6 |
| 2007/0209950 A1* | 9/2007 | Althaus et al. ................ 205/792 |

OTHER PUBLICATIONS

Nriagu et al. "Lead Levels in Blood and Saliva in a Low-Income Population of Detroit, Michigan", International Journal of Hygiene and Enviromental Health, vol. 209 (2006) pp. 109-121, available online Jan. 27, 2006.*
Thaweboon et al. "Lead in Saliva and its Relationship to Blood in the Residents of Klity Village in Thailand", Southeast Asian Journal of Tropical Medicine and Public Health, vol. 36 (2005) pp. 1576-1579.*
Koh et al., "Can salivary lead be used for biological monitoring of lead exposed individuals?", 2003, Occupational and Enviromental Medicine vol. 60 pp. 696-698.*
Nriagu et al. "Lead levels in blood and saliva in a low-income population of Detroit, Michigan", http://www.ncbi.nlm.nih.gov/pmc/articles/PMC1819402/, publsihed online Jan. 27, 2006.*

* cited by examiner

*Primary Examiner* — Robert Kim
*Assistant Examiner* — Nicole Ippolito Rausch
(74) *Attorney, Agent, or Firm* — Gifford, Krass, Sprinkle, Anderson & Citkowski, P.C.; Mark D. Schneider

(57) ABSTRACT

A method for determining heavy metal loading in a subject includes collecting a saliva sample from the subject containing a concentration of a heavy metal. The saliva sample is subjected to inductively coupled plasma mass spectrometry to yield a heavy metal loading measurement for the subject. The saliva sample is readily collected on a substrate absorbing a preselected amount of saliva such as filter paper. As the amount of saliva necessary to saturate a given volume of substrate is known, the volume of saliva within a substrate is also known. The resulting heavy metal loading measurement is readily correlated with a blood level for the heavy metal in the subject.

11 Claims, 3 Drawing Sheets

SALIVA ASSAY TECHNIQUE FOR HEAVY METAL

CROSS-REFERENCE TO RELATED APPLICATIONS

This application claims priority of U.S. Provisional Patent Application Ser. No. 60/776,626 filed Feb. 24, 2006, which is incorporated herein by reference.

FIELD OF THE INVENTION

The present invention in general relates to determining the quantity of heavy metal within an organism and in particular to a noninvasive saliva assay for heavy metal.

BACKGROUND OF THE INVENTION

Heavy metal poisoning remains a public health concern despite efforts to eliminate heavy metal usage. While efforts to remove tetraethyl lead from gasoline, paint and other consumer products have helped reduce body loading of lead, environmental exposure to lead persists in paint chips, dust and lead-containing kitchenware such as glass, ceramic glazes and metallic foils.

Mercury represents another heavy metal that tends to bioaccumulate. Mercury exposure has been traced to contaminants found within coal and are noted to bioaccumulate, especially in fish.

The symptoms of heavy metal poisoning are well known, including especially deleterious effects suffered by children. Upon identification of high heavy metal loadings within an individual, lifestyle changes and the administration of chelation agents serve to minimize the deleterious effects. However, these treatments can only be put in place after testing of an individual for heavy metal.

While various public health organizations and agencies have been successful in performing universal and routine testing of children for heavy metal poisoning, large numbers of individuals are never tested or tested at a frequency that is less than ideal. Compliant testing for heavy metals has met with limited success owing in part to the necessity for a blood draw requiring skilled personnel, parental consent, blood draw trauma to the child, and sophisticated infrastructure to process samples. Saliva has previously been studied as an attractive alternative bodily fluid for the measurement of heavy metal concentrations. However, attempts to correlate salivary lead with that found in blood, bone marrow or fatty tissue have proven inconsistent.

Thus, there exists a need for a saliva-based assay for heavy metals in order to increase screening, especially of children. Additionally, there exists a need for a reproducible saliva sample collection methodology to facilitate correlation between blood and saliva heavy metal concentrations.

SUMMARY OF THE INVENTION

A method for determining heavy metal loading in a subject includes collecting a saliva sample from the subject containing a concentration of a heavy metal. The saliva sample is subjected to inductively coupled plasma mass spectrometry to yield a heavy metal loading measurement for the subject. The saliva sample is readily collected on a substrate absorbing a preselected amount of saliva such as filter paper. As the amount of saliva necessary to saturate a given volume of substrate is known, the volume of saliva within a substrate is also known. The resulting heavy metal loading measurement is readily correlated with a blood level for the heavy metal in the subject.

BRIEF DESCRIPTION OF THE FIGURES

The present invention is detailed with respect to the following figures which show representative and nonlimiting attributes of the present invention.

DETAILED DESCRIPTION OF THE PREFERRED EMBODIMENTS

Figure 1:
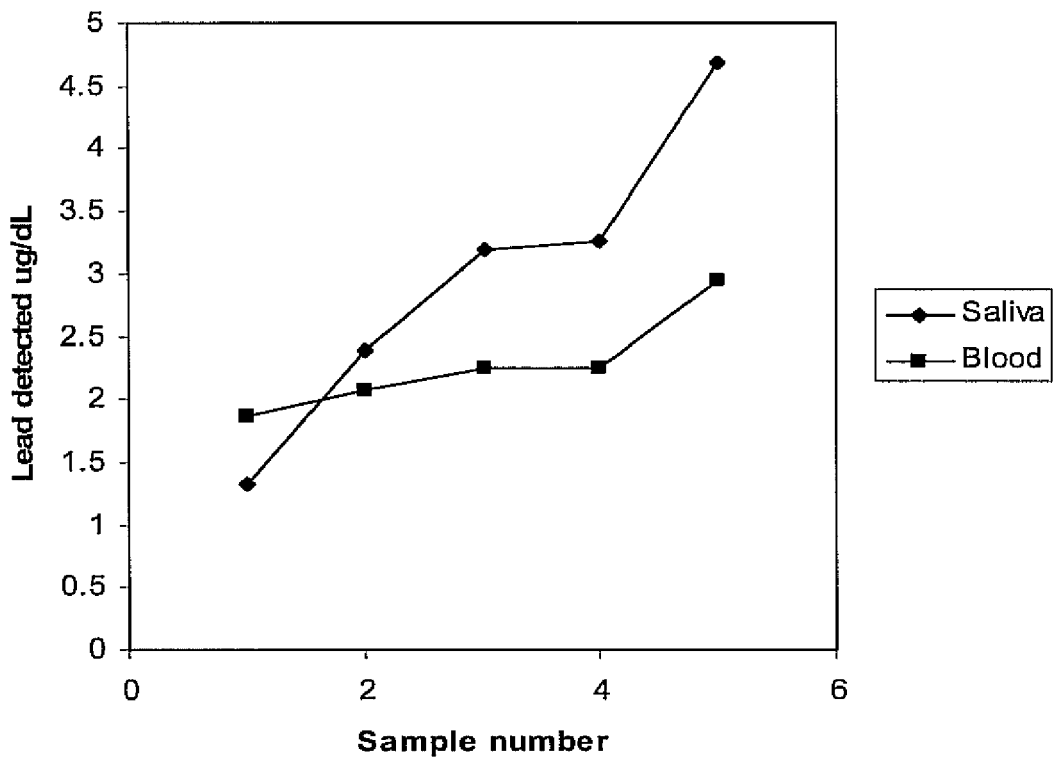
FIG. 1 is a plot of lead levels as measured in micrograms per deciliter according to the present invention for 5 double-blind samples as determined by inductively coupled mass spectrometry.

The present invention has utility as a noninvasive method of determining heavy metal levels within an individual subject. The present invention provides information about heavy metal within an individual subject from saliva in contrast to prior art techniques that have relied on invasive sample collection techniques associated with collection of blood or tissue biopsy. The collection of saliva affords considerable advantages in requiring less skill and precaution in the collection of the sample as compared to blood or biopsy samples. The present invention in establishing a reliable correlation between blood and saliva concentration of a heavy metal has overcome the inconsistencies associated with prior art saliva detection methodologies.

As used herein a "subject" is defined to include a mammalian or avian creature specifically including a human, cow, horse, sheep, dog, cat, and chicken. While the collection of a saliva sample as detailed hereafter is in regard to a human subject, it is appreciated that other saliva samples are readily obtained from nonhuman subjects.

Saliva collection is performed according to the present invention in any number of conventional procedures. Saliva is readily collected in a vial, with an absorbent swab, or pipetted from the buccal cavity onto an absorbent substrate. The simplicity of collecting a saliva sample allows for an untrained individual to collect such a sample. Preferably, the sample is brought into contact with a preservative so as to maintain the saliva sample integrity during transport to a measurement facility. Saliva sample collection techniques and preservatives operative herein are detailed in U.S. Pat. No. 5,968,746.

In an alternative embodiment, a kit is provided for saliva collection that includes a pipette and a piece of filter paper. The pipette is inserted into an individual's mouth and a sample of saliva collected. Optionally, a salivation stimulating substance coats the pipette tip. The saliva stimulating substance illustratively includes ascorbic acid, citric acid, and other known stimulants. With the collection of at least approximately 0.3 milliliters of saliva within the pipette, the saliva is expelled onto the filter paper. Optionally, the filter paper is treated with a substance that delineates the boundaries of a droplet of saliva thereon. A boundary delineating substance illustratively includes starch, a pH indicator, and a vegetable dye. The filter paper has a known volume saliva absorption per unit area and as such, a measurement of a heavy metal from a preselected unit area of filter paper correlates with concentrations in saliva of the investigated method. Saliva dried onto filter paper is readily eluted and measured for the amount of heavy metal found therein.

Regardless of the method of saliva collection, the sample is placed in a bioseal package and assigned a chain of custody number corresponding to the sample. Preferably, the sample is collected in the form of an absorptive paper strip with a predetermined quantity of test strip paper being removed from the test strip and placed into a sample preparation bottle. The predetermined amount of saliva saturated test strip is placed in a quantity of medical grade nitric acid within the sample preparation bottle with the test strip allowed to digest for a predetermined amount of time. By way of example, a 1 centimeter square area of saliva saturated test strip immersed in 5 milliliters of 20% nitric acid is adequately digested after approximately 20 minutes. The sample preparation bottle contents are then removed, optionally filtered and inserted into vials corresponding to predetermined positions with sample coating facilitating correlation of results with the sample.

The sample solution is then drawn into an inductively coupled plasma (ICP) mass spectrometer (MS) (ELAN DRCe ICP mass spectrometer, PerkinElmer). The ICP MS uses the inductively coupled plasma to superheat elements passing through the sample analysis chamber to destroy any molecular bonds and ionize the residual atoms. This liquid sample is formed as an aerosol through application of a vacuum prior to encountering the plasma in preference to air entrainment to form an aerosol so as to enhance signal-to-noise ratio. The ions formed through exposure to the plasma travel through a quadrapole mass spec modulated to collect isotope ions associated with the heavy metal of interest. By way of example, lead isotopes 206, 207, 208 masses have a natural abundance of approximately 24:22:52 atomic percent in addition to providing a quantitative measure of lead within the sample also provides an identity signature when isotope percentages correspond with a particular exposure such as that found in specific industrial working arenas. A similar correlation can be made for mercury isotopes having masses 198, 199, 200, 201, 202 and 204 that have atomic percent natural abundance of about 10:17:23:13:30:7. According to the present invention, heavy metal ions are readily detected as low as single parts per trillion with statistically significant values being obtained within the order of 10 to 30 parts per trillion. As heavy metal concentrations in blood are typically measured in micrograms per deciliter, ICP MS is about three orders of magnitude greater in sensitivity than the 10 parts per million of lead that corresponds to a microgram per deciliter.

Heavy metals detectable according to the present invention are appreciated to be readily identified within a single scan merely by modulating the mass spectrometer to collect particular mass species. Heavy metals readily detectable according to the present invention illustratively include vanadium, chromium, manganese, cobalt, nickel, copper, arsenic, technetium, ruthenium, rhenium, cadmium, tin, antimony, lanthanide series, osmium, mercury, thallium, and combinations thereof.

Intermediate between spectral collection, the system is purged with solvent and periodic calibration standards.

Correlative analysis between the amount of a heavy metal present in a blood sample and saliva sample from the same subject is possible because blood and saliva are made from the same extracellular fluid. The fluid matrix that carries eosinophils, neutrophils and nutrients via the circulatory system also carries enzymatic proteins within the digestive tract. Saliva differs from blood in having a higher water content and shorter circulatory life. As a result, saliva contains less of a heavy metal than the corresponding volume blood sample and additionally saliva represents a better indicator of recent exposure to high levels of a heavy metal associated with residual lead from sources such as diet) environment or inhalation. Upon ingestion of a heavy metal, it is diluted to the bloodstream to a volume of approximately 7 liters for an adult human subject or other extracellular fluid such as saliva to a volume of approximately 10 milliliters. Heavy metal is often known to leach into the tissues of the mouth and throat to afford a measurement indicating a toxic heavy metal content for the subject that is not as readily found by blood heavy metal analysis. As a result, saliva testing allows chelation treatment to be performed before heavy metal has fully entered the bloodstream and been carried to bone marrow or adipose tissue from which removal is problematic.

The present invention is further detailed with respect to tie following nonlimiting examples.

EXAMPLE 1

Stock Solutions

HPLC grade water is purchased from Pharmco and used for up to 12 months after receipt. Each bottle of HPLC grade water when opened is used for only up to 30 days. A 20% nitric acid solution is created by half filling a 1 liter volumetric flask with HPLC grade water and adding 287 ml of 69.7-70% assay trace metals grade nitric acid to the flask and filling to a volume of 1 L. Mass spectrometer wash solvent is provided using HPLC grade water to flush lines.

Clinical standard lead is purchased from VWR International at 1000 ppm, 100 ug/dl. Linearity standards are prepared at 2, 10, 50, 100, and 500 parts per million (ppm) with volumetric glassware and HPLC grade water. A PerkinElmer ELAN DRCe inductively coupled plasma mass spectrometer is energized and allowed to stabilize for from 60 to 90 minutes. Thereafter, the instrument is prompted to load the lead detection protocol setting appropriate parameters for the lead isotopes 206, 207, and 208. Sample times and rinse times for samples set to a preselected level and calibration standards are run using lead calibration linearity standards at 2, 5, 10, 50, 100, and 500 ppm to establish a correlation coefficient of greater than 0.999. A test sample is then run to verify integration parameters. A reservoir is then filled with HPLC grade water and a sample tray of a PerkinElmer 192 Auto Sampler is loaded and programmed to run settings and tray positions for the Auto Sampler that correspond to sample and standard positions. The Auto Sampler is then allowed to provide samples and standards to the ICP mass spectrometer.

This process has been extended and validated for the analysis of a range of heavy metals detailed herein in blood or saliva. The method is calibrated in a range from 0.2 ug/dl to about 50 ug/dl. Samples with higher concentration than the linear range samples should be diluted and rerun as extrapolated data results are considered to be suspect.

Results are calculated from the calibration curve after verifying that all the controls are in the acceptable range and the correlation coefficient of greater than 0.999 is obtained. Saliva values are corrected for diluted factor based on the amount of saliva that can be absorbed into a 1 cm² piece of filter paper. Positive samples are flagged for resampling and notification of health authorities.

To assure peak response for each standard is within ±25% of the expected value. Each peak response is then calculated and entered into an appropriate peak log with all peak logs plotted on a monthly basis along with acceptable high and low ranges. High and low controls are calculated to heavy metal levels within 5% of the expected values. All control results are entered into control result logs and plotted on a trend plot on a routine basis such as weekly. All controls that fall outside of the expected range, the entire sample set are rerun after corrective actions have been taken with concert notation as to corrective actions being documented and the motivations therefor. Controls and standards are run at the beginning and end of each sample set with one control and one blank being run after each 10 samples.

In order to establish a correlation between inventive saliva testing and conventional whole blood lead level testing, a series of 14 blind samples were collected of whole blood and corresponding saliva samples. FIG. 1 depicts saliva measured corresponding blood lead level in micrograms per deciliter for the 14 samples as well as the lower value of the blood lead level determined by conventional techniques. The range of blood low and high levels is also provided in FIG 1.

EXAMPLE 2

Figure 2:
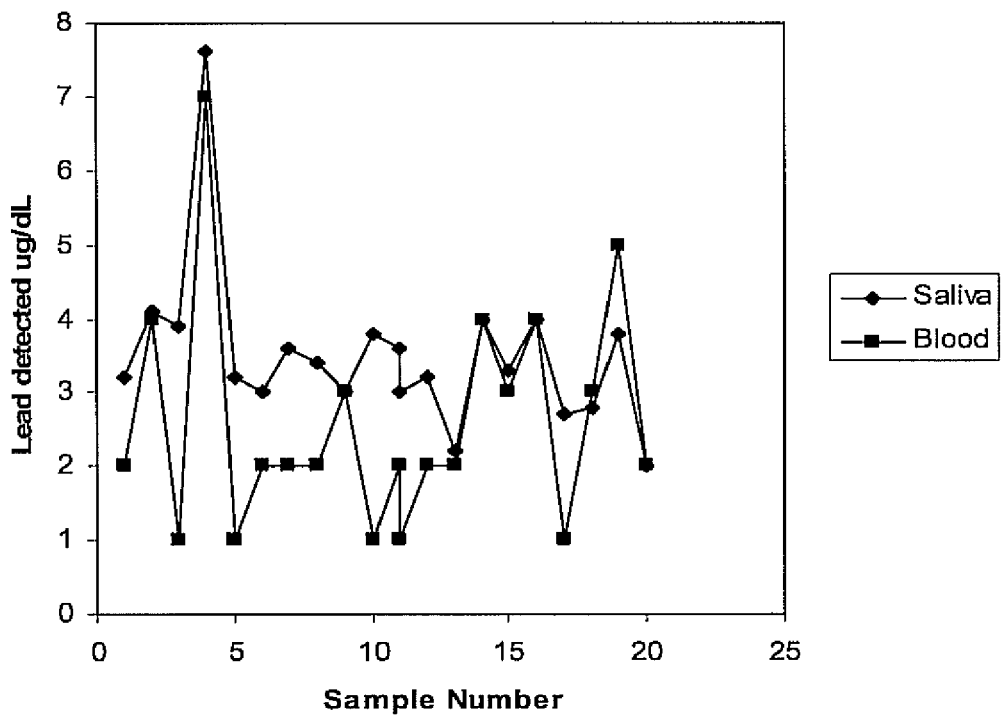
FIG. 2 is a plot of lead level in micrograms per deciliter for 21 double-blind samples after correction for the dilution of lead in saliva relative to blood.

Correspondence of Blood and Saliva Lead Levels Derived from Inductively Coupled Plasma Mass Spectrometry Twenty-one double-blind sample sets were collected from volunteers. Each sample set included a whole blood sample and a saliva sample. Applying the procedure of Example 1, and accounting for dilution associated with saliva absorption into filter paper used to collect the saliva sample, a blood lead level is plotted directly in FIG. 2 for the 21 blind samples while the blood level derived by correcting for saliva dilution associated with saliva absorbable into a square centimeter of filter paper is provided in FIG. 2.

EXAMPLE 3

Correlation of Blood and Saliva Results Including Dangerous Levels of Lead

Figure 3A:
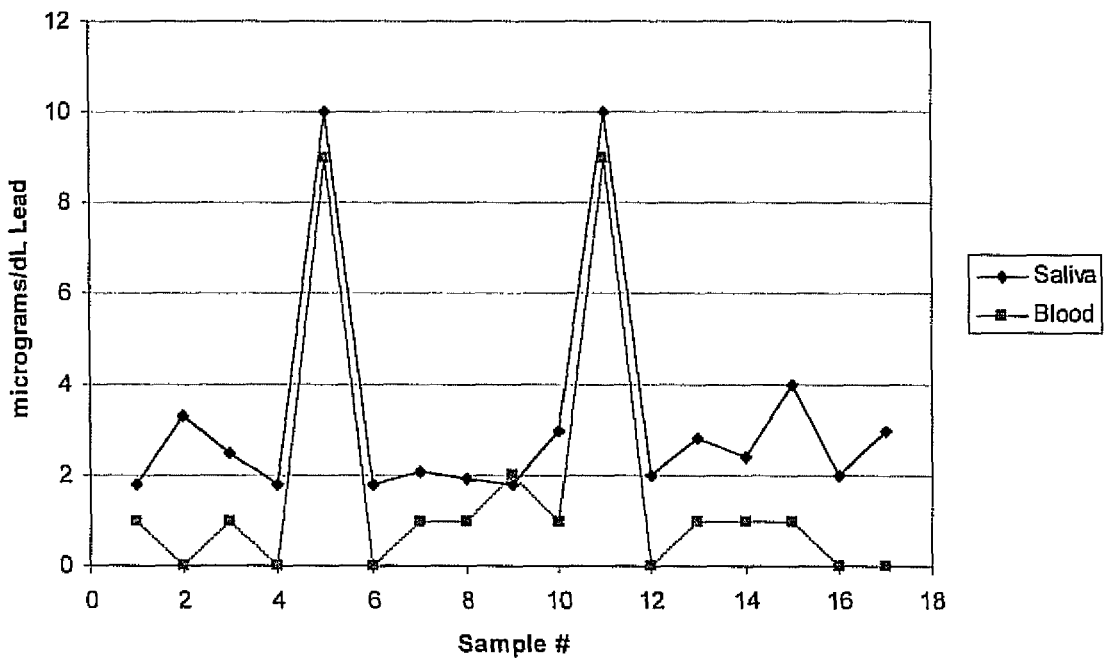
FIG. 3A is a plot of lead level in micrograms per deciliter corrected for saliva dilution for baseline tolerable levels of lead along with 2 samples, 5 and 11, indicating lead levels that have reached a dangerous level.
Figure 3B:
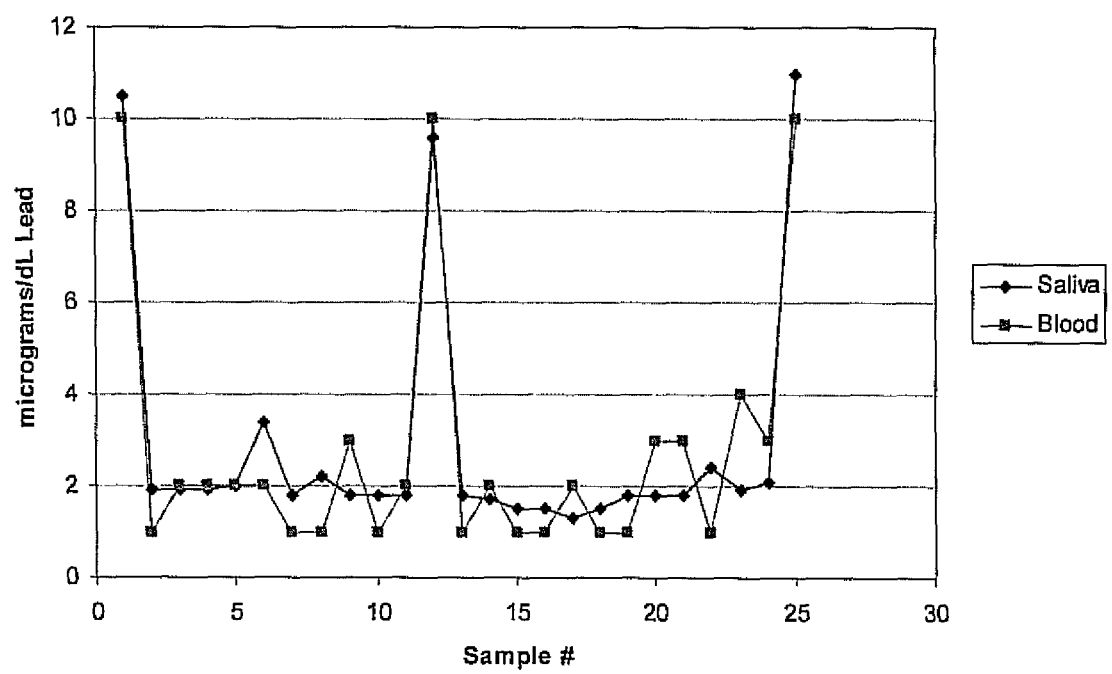
FIG. 3B is a plot of lead level in micrograms per deciliter for double-blind sample sets on 25 samples, one each of saliva and blood.
Figure 4:
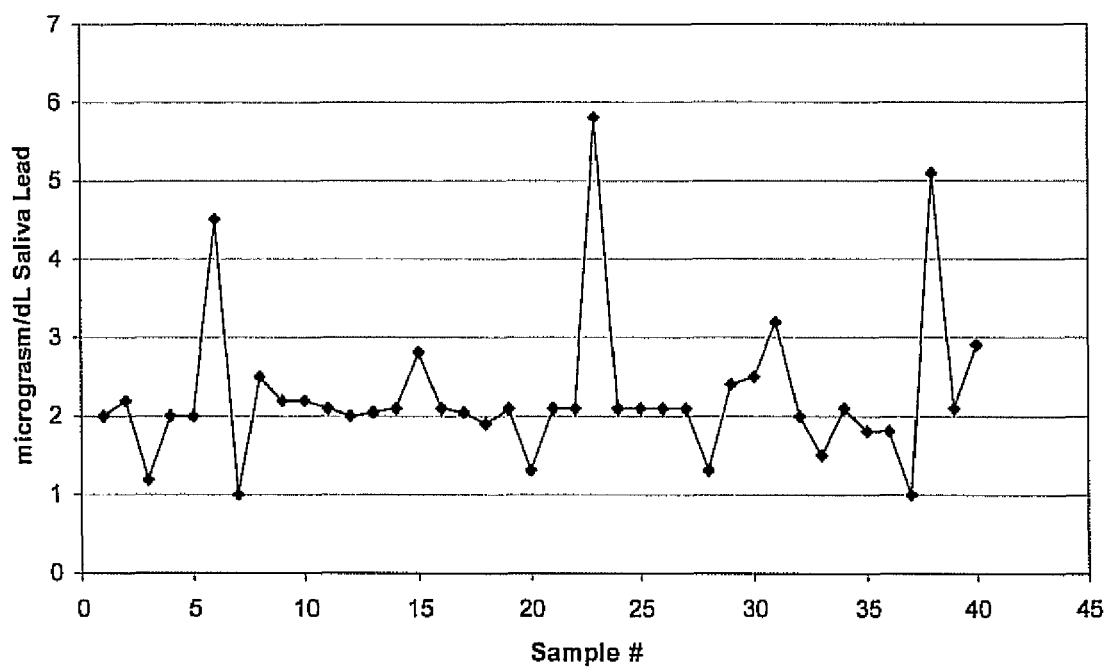
FIG. 4 is a plot of lead level in micrograms per deciliter normalized to that expected to be found in blood based on saliva sampling for 39 double-blind saliva tests.

The sampling procedure of Example 1 is repeated with 17 and 25 dual sets of double-blind saliva and whole blood samples. The results measured lead levels corresponding to blood levels are plotted in FIGS. 3A and 3B, respectively, for the 17 and 25 double-blind sample sets with correction being made for the amount of saliva being absorbable into 1 cm² of filter paper as the saliva collection medium. Based on the high degree of correlation between blood levels detected in blood and saliva, blood levels are estimated from saliva for a group of 39 unknown samples, as shown in FIG. 4.

EXAMPLE 4

Comparison of Blood and Saliva Analysis by ICP Mass Spectrometry

Five sets of double-blind samples each including conventional blood draw and a 1 cm² piece of filter paper saturated with saliva were analyzed by ICP mass spectrometry according to the procedure of Example I with the results plotted in FIG. 5 as measured directly without correlation for saliva dilution and absorption into a quantity of filter paper. Even without correlation, the general agreement is noted between saliva and blood samples.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof The following claims, including all equivalents thereof, are intended to define the scope of the invention.

The invention claimed is:

1. A method for determining heavy metal loading in a subject comprising:
collecting a saliva sample from a subject onto a substrate, said saliva sample containing a concentration of a heavy metal;
subjecting said saliva sample to inductively coupled plasma mass spectrometry to yield a saliva heavy metal loading measurement for the subject from the saliva sample, said saliva heavy metal loading measurement correlating to a blood level of said heavy metal from a blood sample from the subject.

2. The method of claim 1 wherein said mass spectrometer is a quadrapole mass spectrometer.

3. The method of claim 1 wherein the saliva sample is collected on a substrate absorbing a preselected amount of saliva.

4. The method of claim 3 wherein the substrate is filter paper.

5. The method of claim 4 wherein said filter paper further comprises an indicator.

6. The method of claim 1 wherein said heavy metal is lead.

7. The method of claim 1 further comprising diluting said saliva sample in a predetermined solution volume prior to said saliva heavy metal loading measurement.

8. The method of claim 7 wherein said solution is aqueous nitric acid.

9. The method of claim 7 further comprising acid digestion of said saliva sample in the solution volume.

10. The method of claim 1 further comprising yielding a second heavy metal loading measurement from said mass spectrometry.

11. The method of claim 1 wherein the blood level is measured by subjecting the blood sample to the inductively coupled plasma mass spectrometry.

\* \* \* \* \*

UNITED STATES PATENT AND TRADEMARK OFFICE
CERTIFICATE OF CORRECTION

PATENT NO. : 8,049,165 B2
APPLICATION NO. : 11/678769
DATED : November 1, 2011
INVENTOR(S) : David Schneider Page 1 of 1

It is certified that error appears in the above-identified patent and that said Letters Patent is hereby corrected as shown below:

Column 4, line 12 delete ")" insert --,--.

Column 4, line 24 delete "tie" insert --the--.

Signed and Sealed this
Twenty-fourth Day of April, 2012

David J. Kappos
*Director of the United States Patent and Trademark Office*